(12) United States Patent
Kislev et al.

(10) Patent No.: US 7,252,642 B2
(45) Date of Patent: Aug. 7, 2007

(54) SEMEN ANALYSIS

(75) Inventors: Abe Kislev, Haifa (IL); Lev Rabinovitch, Kiryat Ata (IL)

(73) Assignee: M.E.S. Medical Electronic Systems Ltd., Caesarea Industrial Park (IL)

( * ) Notice: Subject to any disclaimer, the term of this patent is extended or adjusted under 35 U.S.C. 154(b) by 474 days.

(21) Appl. No.: 10/478,251

(22) PCT Filed: May 24, 2001

(86) PCT No.: PCT/IL01/00475

§ 371 (c)(1),
(2), (4) Date: Nov. 20, 2003

(87) PCT Pub. No.: WO02/095375

PCT Pub. Date: Nov. 28, 2002

(65) Prior Publication Data

US 2004/0146848 A1 Jul. 29, 2004

(51) Int. Cl.
G21N 21/00 (2006.01)
C12M 3/00 (2006.01)
G21N 21/31 (2006.01)

(52) U.S. Cl. ............... 600/578; 600/579; 422/82.05; 435/288.7

(58) Field of Classification Search ............... 600/578, 600/579; 422/82.05; 435/288.7
See application file for complete search history.

(56) References Cited

U.S. PATENT DOCUMENTS

| | | | |
|---|---|---|---|
| 4,088,448 A | 5/1978 | Lilja et al. | |
| 4,176,953 A | 12/1979 | Bartoov et al. | |
| 4,896,967 A | 1/1990 | Douglas-Hamilton et al. | |
| 4,937,461 A | 6/1990 | Traina | |
| 5,402,240 A | 3/1995 | Thistlethwaite et al. | |
| 6,001,307 A * | 12/1999 | Naka et al. | 422/81 |
| 6,171,850 B1 * | 1/2001 | Nagle et al. | 435/286.1 |
| 6,409,832 B2 * | 6/2002 | Weigl et al. | 117/206 |
| 6,426,213 B1 * | 7/2002 | Eisenson | 435/288.7 |
| 6,660,527 B2 * | 12/2003 | Stroup | 436/165 |

FOREIGN PATENT DOCUMENTS

| | | |
|---|---|---|
| DE | 197 13 249 | 10/1998 |
| EP | 0 905 506 | 3/1999 |
| GB | 2 130 718 | 6/1984 |
| JP | 10185814 | 7/1998 |

OTHER PUBLICATIONS

Tosaka et al. Optical in situ monitoring of silicon diaphragm thickness during wet etching J. Micromech. Microeng. 1995, 5:41-46.*

* cited by examiner

Primary Examiner—Jill Warden
Assistant Examiner—Paul Hyun
(74) Attorney, Agent, or Firm—The Nath Law Group; Gary M Nath; Susanne M Hopkins

(57) ABSTRACT

A method for measuring the total sperm concentration (TSC) in a sample is described and includes: (i) placing the sample in a transparent container between a synchronically pulsed light source and a photodetector; and (ii) measuring the optical absorbance of the sample in the range of 800–1000 nm, the TSC of the sample being proportional to the absorbance. Also described is a sampling device for use in optically analyzing a biological fluid, a method for measuring motile sperm concentration (MSC) in a semen sample, a method of determining the average velocity (AV) of sperm cells and a system for analyzing semen quality including means for measuring TSC, means for measuring MSC; and a video visualization system.

8 Claims, 7 Drawing Sheets

SEMEN ANALYSIS

This application is filed under 35 U.S.C. §371 from International Application No. PCT/IL01/00475, bearing an International Filing date of May 24, 2001.

FIELD OF THE INVENTION

This invention relates to semen analysis.

BACKGROUND OF THE INVENTION

According to WHO statistics, 8-10% of all married couples consult medical professionals after failing to conceive. Over 40 million couples are currently being treated for infertility. Among these infertile couples, it is estimated that the infertility in 40% of the couples is due to male originating causes, and another 20% is due to combined male and female originating causes. Semen analysis is a major technique in evaluating male originating causes.

Standard semen analysis protocol involves the determination of at least three major semen parameters:

1. total sperm concentration (TSC);
2. percentage of motile sperm; and
3. percentage of normal sperm morphologies.

For all practical purposes, semen analysis, a key factor in human male fertility medicine, has not changed since the 1930's and is still done today by microscopic inspection. In fact, it is one of the very few remaining in vitro, body fluid analysis still performed almost solely via manual methods.

This manual methodology involves carefully observing the sperm cells, counting them to determine their concentration, classifying their motility, identifying their morphology, etc. This work requires high expertise, is very labor intensive and if done according to standard protocols, takes at least an hour per test.

Manual assessments are known to be quite inaccurate due to numerous sources of error. The main sources of error are:
Subjectivity of the observer.
The varying criteria used in the different labs and by different observers.
The large statistical errors due to the limited number of sperm analyzed.

The WHO manual (*WHO laboratory manual for the examination of human semen and sperm-cervical mucus interaction.* 4$^{th}$ edition, Cambridge University Press, 1999) recommends observing not less than 200 sperm and classifying the morphology and motility of each. This itself is an error introducing procedure due to the tediousness and time consuming nature of the task. In practice, 50 to 100 sperm cells at most are analyzed. Even if the observer introduces no errors, the statistical error alone reaches tens of percentages.

As a result of the above methodology, semen analysis test results are globally recognized to be highly subjective, inaccurate and poorly reproducible. Inter lab and inter technician variations are of such proportions that this issue is of major concern in male fertility medicine and the unresolved subject of discussion in the vast majority of symposiums, congresses and conventions on the subject.

In order to overcome these difficulties, medical instrumentation companies have introduced dedicated computerized systems based on image analysis (CASA—Computer Assisted Semen Analyzers). These systems require an extremely high quality image because all their results are based on image processing. Although these systems have attempted to replace manual analysis and establish industry accepted standards, they have not succeeded in either of these objectives.

The first objective could not be achieved because analysis results continue to be dependent on manual settings and on the different makes of equipment. Replacing routine manual analysis is totally impracticable because the systems are extremely expensive, complex and difficult to use. The fact is that such systems are generally not found in routine semen analysis but have rather established their niche almost solely in research centers, university hospitals and occasionally in highly specialized fertility centers.

An additional approach for semen measurements is described in U.S. Pat. Nos. 4,176,953 and 4,197,450, whose entire contents are incorporated herein. These patents describe a method for measuring sperm motility using electro-optical means and an analog signal analyzer. A suspension of sperm cells is continuously examined in a predetermined field in order to detect variations in optical density by the motion of the sperm. An amplitude-modulated analog electrical signal is generated in response to the variations, and the peaks and valleys of this signal are counted over a predetermined time period to provide an abstract parameter termed Sperm Motility Index (SMI). This parameter is related to motility and gives readings which are proportional to the number of motile cells multiplied by their respective velocity.

An automatic sperm analyzer called the Sperm Quality Analyzer (SQA), which provides the SMI parameter, has been on the market for a number of years. The analyzer is used in the following manner: a sperm specimen is taken up by a disposable chamber which has a rubber bulb at one end to aspirate the sample, and a thin measuring compartment at the other end. After aspirating the sample, the measuring compartment is inserted into the SQA and the SMI of the sample is automatically determined. The SMI parameter, although useful in some applications, was not significantly accepted by the medical community as a viable alternative to the conventional microscopic semen measurements.

It is common knowledge that in some fields of veterinary fertility analysis, total sperm concentration (TSC), is evaluated by measuring optical turbidity of the specimen. The physical principle behind this approach is that sperm cells are more opaque than the surrounding seminal plasma, and absorption of a light beam by the specimen is therefore proportional to the TSC.

For example, U.S. Pat. No. 4,632,562 discloses a method of measuring sperm density by measuring the optical absorbance of a sperm containing sample and relating the absorbance output signal to the density by using at least three summing channels. The disclosed method is intended for use in artificial insemination in the cattle breeding industry, and measures the optical absorbance in the range of 400-700 nm.

This technology however, has not and could not be adopted for human use for the following reasons:

(1) Human sperm concentrations in the normal range (and even in higher than normal cases), are more than an order of magnitude lower than in most of their veterinary counterparts—where this technology has been adopted.

(2) Human cases are treated even when sperm concentrations are far below their normal levels. This of course is not the case for animals. Infertile animals are normally culled—in any case, they are not treated for infertility.

(3) TSC in humans is a parameter, which in itself, is totally insufficient for fertility investigations, and microscopic analysis is in any case required for all the other data in the standard semen analysis protocol. To a large degree, this also holds for veterinary applications. This fact made optical absorption measurements superfluous, and no real effort has been invested in this field.

There is thus a need for a simple, objective technique for measuring TSC in human semen.

According to the WHO manual, sperm motility assessment (considered by most to be the most important single semen parameter) can be carried out manually using a grid system under the microscope or, alternatively, by use of CASA.

CASA provides some advantages over manual methods. However, accuracy and provision of quantitative data are totally dependent on precise semen preparation techniques and instrument settings. These factors (high expertise and sophisticated environment) along with the prohibitive cost of such instrumentation, rule out for all practical purposes their application for routine semen analysis.

U.S. Pat. No. 4,896,966 discloses a motility scanner for characterizing the motion of sperm, bacteria and particles in fluid. The scanner comprises an optical system including a collimating lens, condensing lens, imaging lens and a pair of reflecting elements, a source of illumination, radiation sensing means, signal processing means, and display means. The imaging lens has a useful depth of field at its object plane of at least about 0.2 mm.

SUMMARY OF THE INVENTION

It is an object of the present invention to provide a method for measuring TSC.

It is a further object of the invention to provide a method for determining the motile sperm concentration (MSC) and % motility.

It is a still further object of the invention to provide a sampling device for use in the determination of semen parameters.

It is another object of the invention to provide a system for the determination of semen parameters.

In a first aspect of the invention, there is provided a method for measuring the total sperm concentration (TSC) in a sample. The method comprises (i) placing the sample in a transparent container between a synchronically pulsed light source and a photodetector; and (ii) measuring the optical absorbance of the sample in the range of 800-1000 nm, the TSC of the sample being proportional to the absorbance.

The method of the invention provides an objective measurement of TSC which is not dependent on image analysis, and which can measure human TSC. However, the method may also be used to measure animal TSC.

In a second aspect of the invention, there is provided a sampling device for use in optically analyzing a biological fluid comprising:
(i) an aspirator for aspirating the fluid into the device;
(ii) a thin measuring chamber having an upper and lower wall, the distance between the walls being in the range of 100-500 microns;
(iii) a thick measuring chamber having an upper and lower wall, the distance between the walls being in the range of 0.5-3 cm; and
(iv) means for excluding air from the measuring chambers.

In a preferred embodiment, the biological fluid is semen, most preferably human semen. The device serves both as a sampler and dual test chamber, enabling simultaneous testing of TSC and MSC. No dilution is required for any of the measurements. This not only saves labor but also eliminates a significant source of errors—namely, dilution inaccuracy.

The device also enables (when required) built-in visualizations of the specimen without transferring it to a separate viewing chamber. The thick chamber is also referred to as an optical densitometer.

In a third aspect of the invention, there is provided a method for measuring motile sperm concentration (MSC) in a semen sample comprising:
(i) placing the sample in a transparent container between a light source and a photodetector, wherein the sperm motion in the sample modulates the light transmitted therethrough, thereby generating a signal;
(ii) sampling the signal so as to produce a plurality of signal samples;
(iii) selecting acceptable signals;
(iv) calculating an absolute value for each of the acceptable signal samples;
(v) calculating an average a of the absolute values; and
(vi) calculating the MSC based on the average a.

It has now been discovered that analysis of waveforms of the analog signals derived from a light beam which traverses a semen sample can provide an indication of the MSC. Using appropriately selected criteria, excellent correlation was found to exist between the averaged area covered by the waveform and the MSC. The MSC of a sperm sample is obtained in accordance with the invention by analyzing optical properties of the sample, which vary over time due to the motility of the sperm. This is in fact, the average signal amplitude in the relevant portions of the waveform, as will be described in more detail below.

In a fourth aspect of the invention, there is provided a method of determining the average velocity (AV) of sperm cells comprising:
(i) obtaining a Sperm Motility Index (SMI) of the sperm cells as defined in U.S. Pat. No. 4,176,953;
(ii) obtaining the MSC; and
(iii) calculating AV using an algebraic expression involving the ratio SMI/MSC.

Reference is made here to U.S. Pat. No. 4,176,953 issued Dec. 4, 1979, and which has been implemented in various versions of Sperm Quality Analyzers produced by Medical Electronic Systems, Israel. This patent, when applied to semen analysis, provides a parameter called SMI (Sperm Motility Index). As disclosed in the above patent and proven in numerous supporting studies, SMI is a function of both the concentration of motile cells (what is referred to as MSC) and their average velocity (AV). For the sake of simplification, we can say that SMI is a function of MSC× AV, or AV is a function of SMI/MSC. The average velocity of a sperm sample can provide an indication of the quality of the motility of the sperm.

Not withstanding that which is stated above, SMI as a function of MSC and AV is more complex than a direct multiplication. After observing, analyzing and measuring over a hundred semen samples, the correct inter-relationship (formula) between them has been developed. In general terms, the formula for extracting the average velocity can be defined as: AV=f(SMI/MSC), "f" being a polynomial of the third degree. Working with $f(x)=1/1000x^3+1/10x^2+0.89x$, provided a correlation factor of r=0.82.

It should be noted that most semen analysis protocols require data on the % of sperm having progressive motility rather than their average velocity. Progressive motility is defined as those sperm having an average velocity of 5 microns/second or more. This parameter too, can readily be extracted from the average velocity if a normal spread of velocities is assumed around the average. Even in cases where the velocity spread is not normal, the error in calculating the % of progressively motile sperm is not significantly affected. Moreover, when different minimal velocities are defined as progressively motile, this varying threshold is readily entered into the calculation, thereby giving extra flexibility in providing this parameter. This is important when working in different diluting media, ambient temperatures or in fact different species in vet measurements.

In a fifth aspect of the invention, there is provided a system for analyzing sperm viability comprising:
(i) means for measuring TSC;
(ii) means for measuring MSC; and
(iii) a video visualization system.

The system of the invention combines the measurement of the two major sperm parameters TSC and MSC, with the traditional visualization of the sperm, thus enabling acquiring the third parameter—sperm morphology. In a preferred embodiment, TSC and/or MSC are determined according to the methods of the invention. In another preferred embodiment, the system further comprises the sampling device of the invention.

It should be emphasized that there is a basic difference between the video visualization system used in the system of the invention and other sperm visualization systems (such as CASA). The other systems require extremely high quality images because all their results are built on image processing. In the present invention, on the other hand, visualization is used only as a complementary tool to view atypical or suspect cases, to add confidence to processed results, to identify specific pathologies and to enable manual sperm morphology assessment, when required.

In order to fulfill these tasks, the video visualization system used in the invention is designed as a compact, inexpensive subsystem, which although of limited use as a stand-alone, precisely fills a complementary role in the system of the invention. An additional important advantage of the visualization system as compared to microscopic procedures, is that pipetting, preparation of slides, dilutions and filling of hemocytometers is unnecessary. Use, together with the video visualization system, of the device of the invention, which doubles as a complete test chamber, obviates all of the above. These features, in effect permit and enable the use of the system of the invention in any small clinic or even office environment.

The video visualization system allows one to obtain the following supplementary information regarding the tested sample:

1. Measurement of Very Low Sperm Concentrations

Measuring TSC at very low concentrations (below 5 million sperm/ml) is inherently limited in accuracy. This is due to the fact that light absorption by factors other than sperm cells, may become relatively significant at these low levels. Light absorption may be due to seminal plasma variability or to the presence of cells other than sperm. The latter include WBCs (white blood cells indicating infections) and other immature or non-spermic cells from various sources, etc. Since according to the invention TSC is measured by optical absorption, without visualization there would be a possibility for ambiguity in the very low ranges due to the above mentioned considerations. When TSC is considered important in the low ranges, visualization enables differentiation between the different cells contributing to the light absorption. Since MSC is measured independently of light absorption, the % motility (MSC/TSC) can be calculated using the visually determined TSC parameter.

2. Identifying Foreign Cells in the Semen

The system is useful in identifying the presence of other cells which may have an effect on semen quality and/or assist in diagnosing patient ailment. For instance, leukocytes indicate infection, immature cells indicate a problem in spermatogenesis, agglutination may be due to a number of causes, etc.

3. Manual Sperm Morphology Assessment

Although the system of the invention automatically assesses the % of sperm with normal morphologies, it does so according to a given criteria (e.g. the WHO criteria). Regretfully this criteria is not universally accepted. Such universally accepted criteria do not yet exist, and are often a factor of application. For example, morphology criteria for IVF and ICSI applications are normally far stricter than in normal cases. Other international standards (such as strict or Krueger criteria) are also widely applied. Visualization allows the fertility practitioner to select his own criteria as well as to identify the specific defects present (head deformity, tail problem, etc.)

4. Vasectomy Validation and Azoospermia Diagnosis

In order to fully validate the outcome of vasectomy or to obtain a conclusive diagnosis of azoospermia, it is necessary to determine that there are absolutely no sperm in the semen under evaluation. This is generally not possible with the light absorption technology, because the concentrations that are to be measured can be very low. In this case, manual visualization is necessary in order to carefully scan large fields of view in search of individual sperm cells. The sperm visualization system used in the system of the invention is specifically tailored to optimally address these applications.

5. Hard Copy

The video visualization system enables "freezing" a given selected view (or a few views) which may then be printed and attached to the Semen Analysis Report. This is of great value for consultations and validation of treatment efficacy. A by-product of the freezing option is viewing the semen sample under static conditions. This strongly facilitates analysis and counting. In microscopic assessments, this can only be done by demobilizing (killing) the sperm prior to viewing. Even then, all dead sperm will end up in one layer, a condition which normally complicates analysis due to high concentration and sperm overlap in the said layer.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE INVENTION

EXAMPLE 1

As stated above, the automatic optical measurement of TSC in human semen samples as opposed to animal samples has been hampered in the past due to the low concentration of sperm cells. This, together with the high background electronic and optical noise due e.g. to seminal plasma variability has prevented the application of methods routinely used in veterinary fertility analysis. The method of the present invention comes to overcome these obstacles by combining the following features:

(i) the sample is placed in a transparent container between a synchronically pulsed light source and a synchronically enabled photodetector. The use of a synchronically pulsed light source and photodetector enables the distinction of sperm cells at low concentrations over electronic noise levels.

(ii) measuring the optical absorbance of the sample in the range of 800-1000 nm. It has been found that measuring the absorbance in the near infrared region provides the optimal conditions for obtaining strong absorption by sperm cells and low absorption by seminal plasma. Preferably the measured range is 850-950 nm. Most preferably, the range is 880-900 nm.

By using the method of the invention, the TSC of a sample may be determined as a function of the absorbance. Although the method of the invention is preferably used with samples of human semen or human sperm, it may also be used with animal semen and animal sperm, preferably after appropriate dilution.

Figure 1:
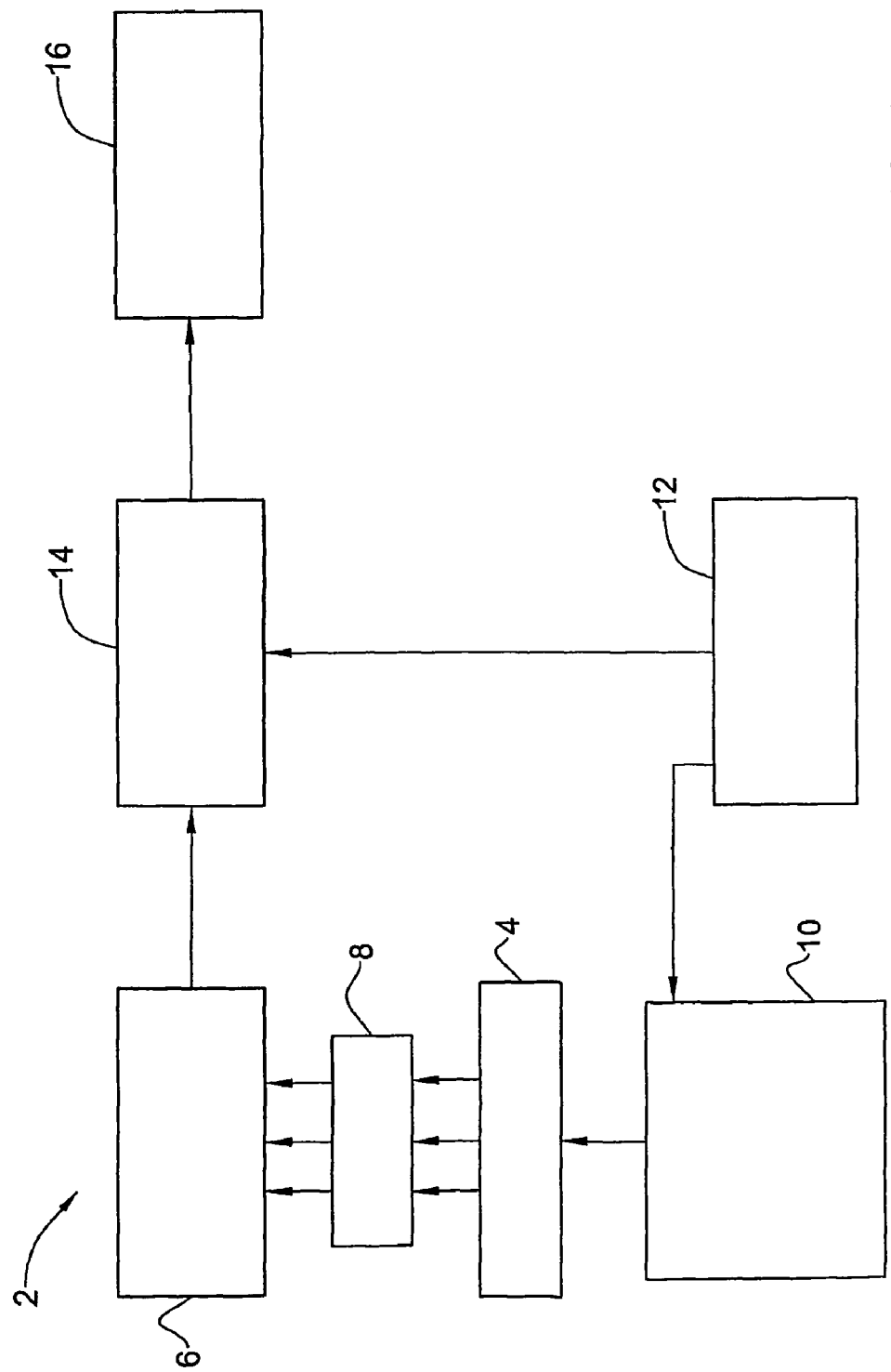
FIG. 1 is block diagram illustrating one embodiment of the method of measuring TSC according to the invention.

An example of an optical system using one embodiment of the method of the invention is illustrated in FIG. 1. The system, indicated generally by the numeral 2, comprises a light source 4, a photodetector 6 and a sample holder 8 interposed therebetween. A preferred light source may be a fast-switching synchronically pulsed light emitting diode (LED) which emits light in the near infrared region. The light source may be controlled by a light intensity controller 10 which in turn is regulated by a modulator 12. The photodetector is capable of detecting synchronically pulsed light. The photodetector transmits the measured analog signals to a demodulator 14, which is also regulated by the modulator 12, and from there to output 16 of the signal in digital form.

The beam path through the sample is preferably vertical. The length of the beam path through the sample is generally between 5 and 15 mm, preferably 10 mm. The sample holder must be fully transparent to light waves in the near infra-red region of between 800 and 1000 nm. The plastic material from which the sample holder is made must be totally non toxic to sperm cells. A preferred material is polystyrene PG-79. The sample holder should preferably be designed to totally prevent penetration and forming of air bubbles in the sample, which interefere with the optical measurement.

By using the method of the invention, TSC detection levels down to appr. 2 million cells/ml. have been achieved. This level already indicates extreme semen pathology.

EXAMPLE 2

Figure 2:
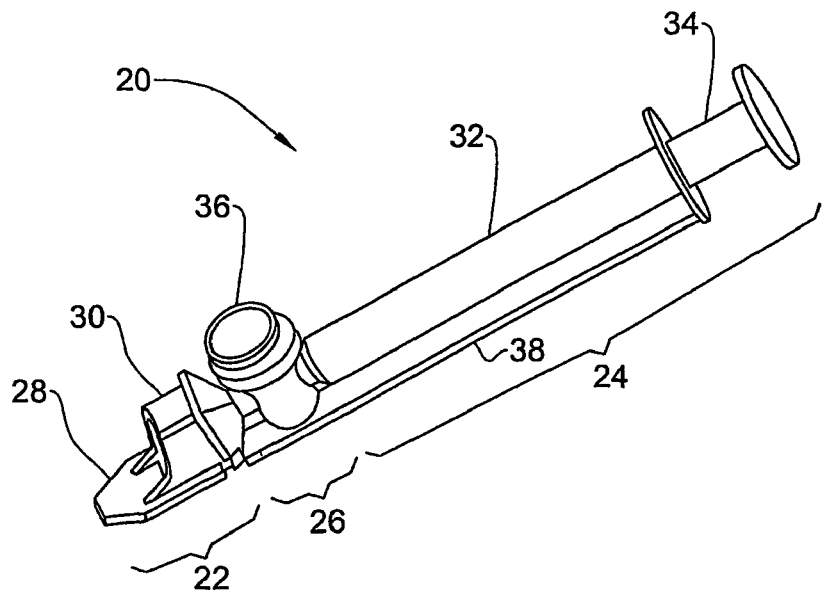
FIG. 2 is a perspective top view of one embodiment of a sampling device according to the invention.

FIG. 2 illustrates one embodiment of a sampling device 20 according to the invention, for use in measuring semen. The device comprises an anterior optical viewing section 22, a posterior aspirating section 24 and an intermediate air exclusion section 26.

The optical viewing section 22 comprises a thin measuring chamber 28 and a thick measuring chamber 30. The thin chamber is used to measure MSC and/or for visualization, while the thick chamber is used to measure TSC. In this way, multiple parameters can be measured simultaneously using the same sampling device and sampling step.

The aspirating section 24 comprises a cylinder 32 and a plunger 34 slidingly inserted therein. These parts match each other and function as in a standard syringe. This section serves for the aspiration of the semen sample into the measuring chambers.

The air exclusion section 26 comprises a separating valve 36 for separation of the measuring chambers from the cylinder volume after filling. The aspirator, thin measuring chamber, thick measuring chamber and air exclusion section are all in fluid communication.

An adapter 38 in the form of a rectangular rail extends along one side of the device 20 and serves for the correct sliding in and aligning of the device upon insertion into an optical instrument by which the sample is evaluated. It also provides the mechanical support and stability required for precision electro-optical measurements.

Figure 3:
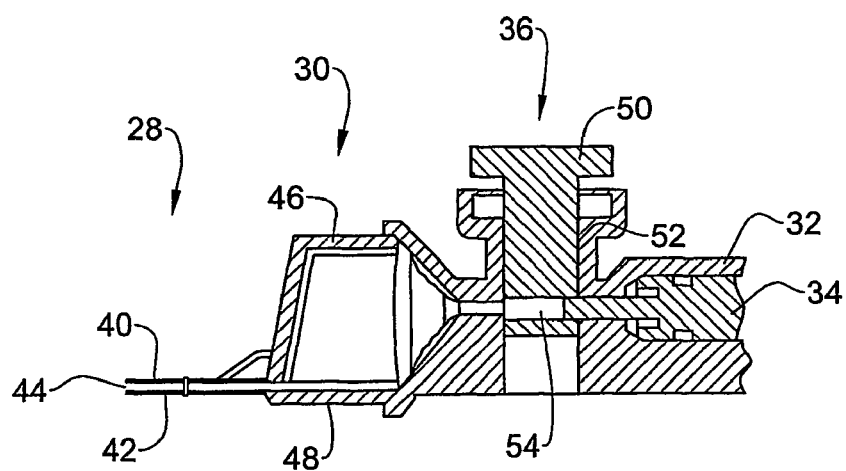
FIG. 3 is a partial side sectional view of the device of FIG. 2.

The parts of the device may be seen more clearly in FIG. 3. The thin measuring chamber 28 is an internal cavity having an upper 40 and a lower 42 parallel transparent wall through which the optical beam may pass. The distance between the walls is in the range of 100-500 microns, preferably 250-350 microns, most preferably approximately 300 microns. In the later case, the volume of liquid in the chamber is approximately 25 µl. The anterior end 44 of the chamber has an aperture through which the sample may be drawn into the device. In the illustrated embodiment, the chamber is approximately 4 mm wide.

The thin measuring chamber serves for evaluation of sperm motility and may be positioned between a light source e.g. opposite the lower wall 42 and a photodetector e.g. opposite the upper wall 40. It will be understood that the light source and photodetector may also be positioned on the opposite sides of the chamber. A light beam is transmitted through the chamber containing a semen sample. The detector on the other side of the chamber registers optical density variations caused by moving sperm cells. The optical density variations are translated into an electrical signal by the photo-detector which is then routed to the electronic circuits to be filtered, digitized and processed so as to indicate the MSC. The thin measuring chamber may also be used with a video visualization system, as will be further explained below.

The thick measuring chamber 30 has an upper 46 and a lower 48 transparent wall through which an optical beam may pass. The distance between the walls is in the range of 0.5-3 cm, preferably 0.8-1.2 cm, most preferably approximately 1 cm. The approximate volume held by the thick compartment in the latter case would be approximately 0.5 ml.

This chamber serves for electro-optical absorption measurements of sperm concentration. A light beam, which may be the same or different from that of the thin chamber 28, is transmitted through the upper and lower walls of the chamber and detected by a photo-detector. The chamber volume should be completely filled with a sperm sample in order to avoid inaccuracies due to air bubbles. The attenuation of the light beam as it passes through the chamber is proportional to the sperm concentration. The light beam intensity is measured after passing through the chamber and translated to units of TSC by electronic means. The order of the chambers in the sampling device may be exchanged.

Figure 4:
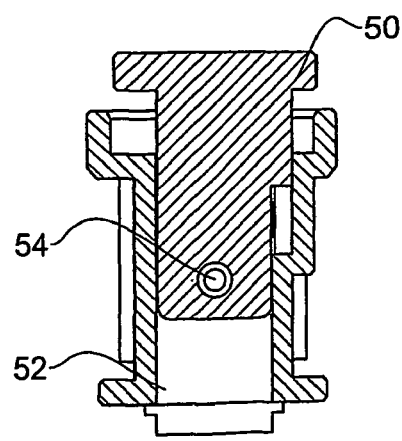
FIG. 4 is a sectional view of the separating valve rotated 90° from the view of FIG. 3.

The cylinder 32 is in fluid communication with the two measuring chambers 28 & 30, so that by drawing the plunger 34, fluid is drawn into the chambers. This method of aspiration allows large sample volumes to be aspirated into the device. In order to prevent air bubbles from remaining in the measuring chambers, a separating valve 36 is interposed between the cylinder and the measuring chambers, and is in fluid communication with them. The valve is shown in detail in FIG. 4 and comprises a piston 50 slidingly held in a valve housing 52. A connecting bore 54 connecting between the measuring chamber 30 and the cylinder 32 passes through the piston 50.

When the valve is in the upper position, there is a connection between the measuring chambers and the aspirating cylinder. Pressing the valve down breaks that connection and ensures that no air remains in the measuring chambers where the samples are measured and no leakage will occur even when there is a temperature variation. This technique is equivalent to positive displacement since air is excluded from the measured fluid volumes (except at the anterior end 44). This design enables working with samples of virtually all viscosities, while at the same time preventing leakage and the penetration of air bubbles into the specimen volumes to be analyzed.

Although the means for excluding air from the measuring chambers has been exemplified by a separating valve, other means may also be used, such as a positive displacement pipette All parts of the device may be manufactured from any material which is not toxic to the measured cells. Preferably, the material is relatively cheap, such as plastic materials, so that the device can be disposable. An example of a polymer which may be used to produce the device is polystyrene PG79. The separating valve, cylinder and piston may be made from polypropylene. The thin measuring compartment is by far the most toxi-sensitive part of the device due to the very high area to volume ratio of the seminal liquid in that section.

In order to aspirate a sample into the device 20, the tip 44 of the thin measuring compartment 28 is dipped approximately 5 mm deep into the semen sample, which is then aspirated into the device past the separating valve 36. Only app. 0.6 cc are required for a complete filling of the device. The separating valve is then pushed down, and the device may be inserted into an optical measuring apparatus.

EXAMPLE 3

Figure 5:
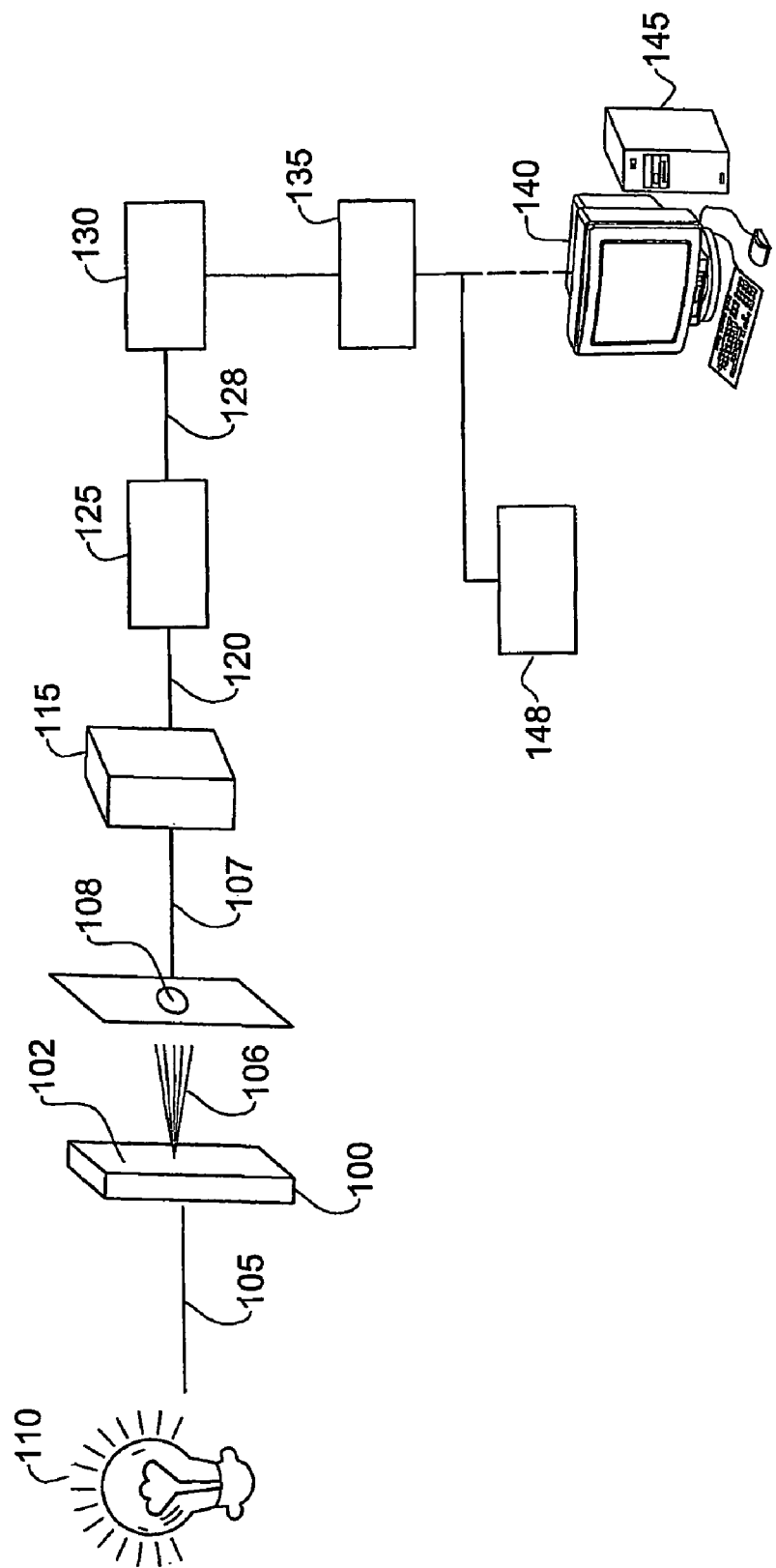
FIG. 5 is a schematic illustration of a system for semen analysis according to one embodiment of the invention.

As mentioned above, determination of the MSC according to the invention requires the generation of a voltage signal which is proportional to the MSC. FIG. 5 shows one embodiment of a system for semen analysis capable of generating such a signal.

Figure 8:
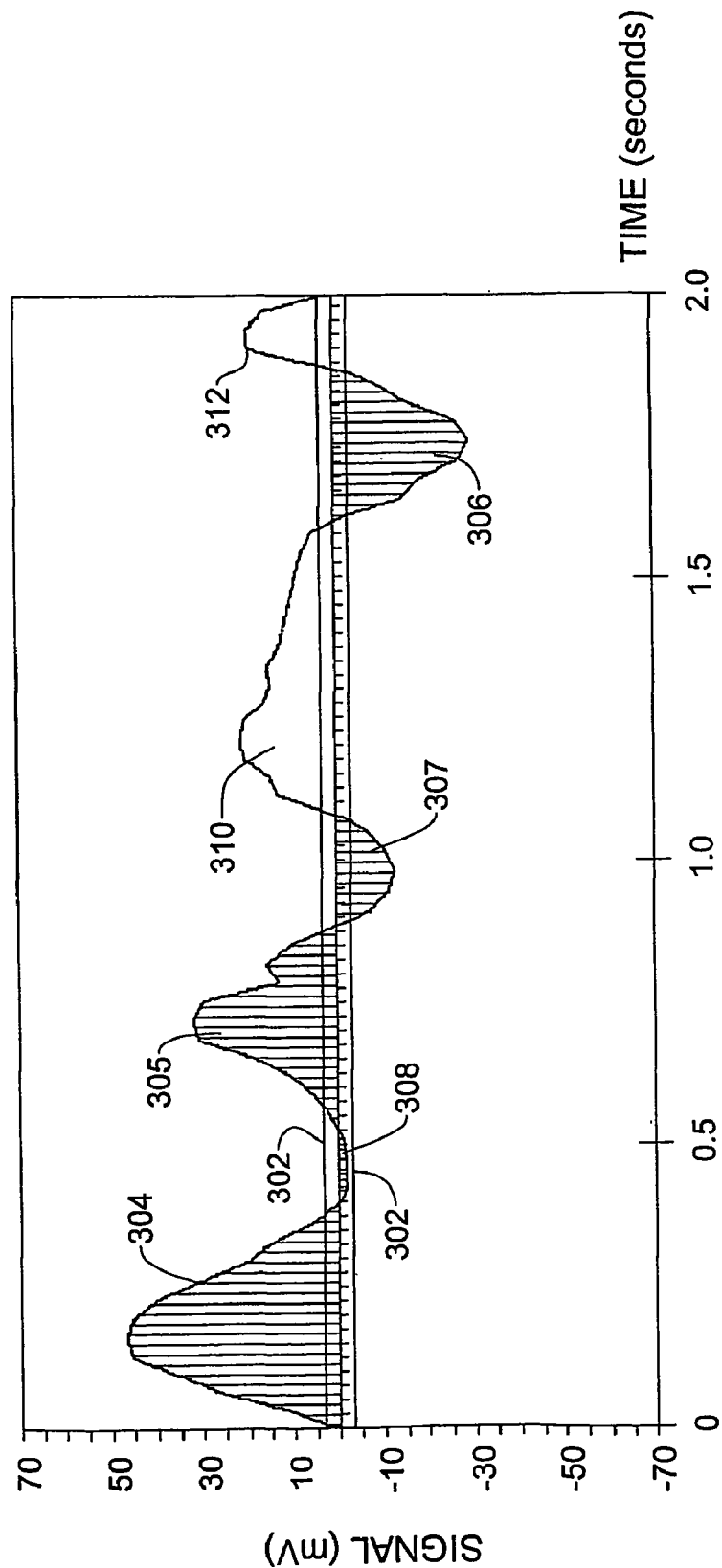
FIG. 8 illustrates a typical analog signal of motile sperm as a function of time.

An optical capillary 100 having a rectangular cross-section is used to hold a semen sample 102. The capillary 100 is illuminated with an incident light beam 105 produced by a light source 110. The capillary 100 has an optical path of 300 μm through which the light beam 105 passes. After passing through the capillary, the scattered beam 106 is collimated by a round aperture 108 having a diameter of 70 μm. The collimated beam 107 impinges upon a photodetector 115. The photodetector 115 produces an analog voltage signal 120 proportional to the intensity of the beam 107. The analog signal varies in time due to the motility of the sperm in the semen sample 102, as shown for example in FIG. 8. The analog signal 120 is inputted to an analog-to-digital converter 125 that samples the analog signal 120 at a rate of e.g. 8000 Hz and generates a digital output signal 128. The digital output signal may be stored in a memory 130. Sperm motion in the sample 102 leads to a modulation in the intensity of the beam 107, which in turn affects the analog signal 120 and digital signal 128.

A processor 135 is configured to carry out an analysis of data stored in the memory 130 in order to produce an analysis of the semen sample 102. The results of the analysis may be displayed on any display device such as a CRT screen 140 of a personal computer 145, or on an internal LCD screen 148 of the measuring device.

Figure 6:
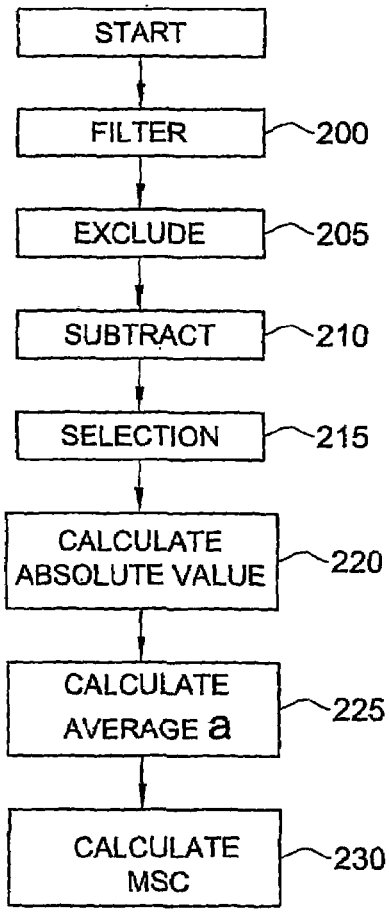
FIG. 6 is a flow chart illustrating an algorithm for calculating the MSC.

FIG. 6 shows a flow chart diagram for one embodiment of an algorithm for calculating the MSC as carried out by e.g. the processor 135 of FIG. 5, in accordance with the invention.

In step 200, the digital signal 128 of FIG. 5 is digitally filtered in order to remove high and low frequencies that are not relevant to the dominant frequency of the signal, which is determined by the motility characteristics of the semen sample 102. This is done in order to optimize the signal to noise ratio. The DC component of the signal 128 is also removed. For human sperm samples, for example, the optimal relevant frequency range was found to be between 5 and 30 Hz. In step 205, digital samples having an absolute value below a first predetermined threshold, which may be determined empirically, are excluded. In step 210 the same threshold value is subtracted from all remaining samples.

In step 215, a waveform selection procedure is carried out to discard all waveforms due to artifacts such as from non-relevant cells, etc. A preferred embodiment of waveform selection with human sperm is to eliminate all waveforms not satisfying the following criteria:

Minimum height—10 millivolts.

Minimum width—37.5 milliseconds.

Maximum width—500 milliseconds.

Minimum rise/fall time—2.5 milliseconds.

The correct definition (and detection) of the beginning and end of sperm associated waveforms are defined as those where significant changes of waveform direction occur. The time difference between two such points defines the time width of a given wave. The manner of selection may be understood by way of example with reference to FIG. 8 (not drawn to scale), which shows the amplitude of the analog signal (120 in FIG. 5) as a function of time. The threshold 302 is determined empirically to provide optimal linearity between the output signal and the microscopically measured MSC. The waveforms that are used for the calculation of MSC are labeled 304, 305, 306 and 307. The other waveforms have been rejected for various reasons: 308 because its peak is less than the threshold; 310 because it is too wide; and 312 because it is too narrow.

In step 220 of FIG. 6 the absolute value of all selected samples is calculated, and in step 225, the average a of the absolute values is calculated. In step 230, the MSC of the sample 102 is calculated based upon the average a. For example, it was found that the dependency of MSC on a can be described by a linear equation of the form:

$$MSC = \alpha a$$

where α is an empirically derived constant. In a preferred embodiment, the dependency of MSC on a may be described by a quadratic equation of the form:

$$MSC = Aa^2 + Ba$$

Figure 9:
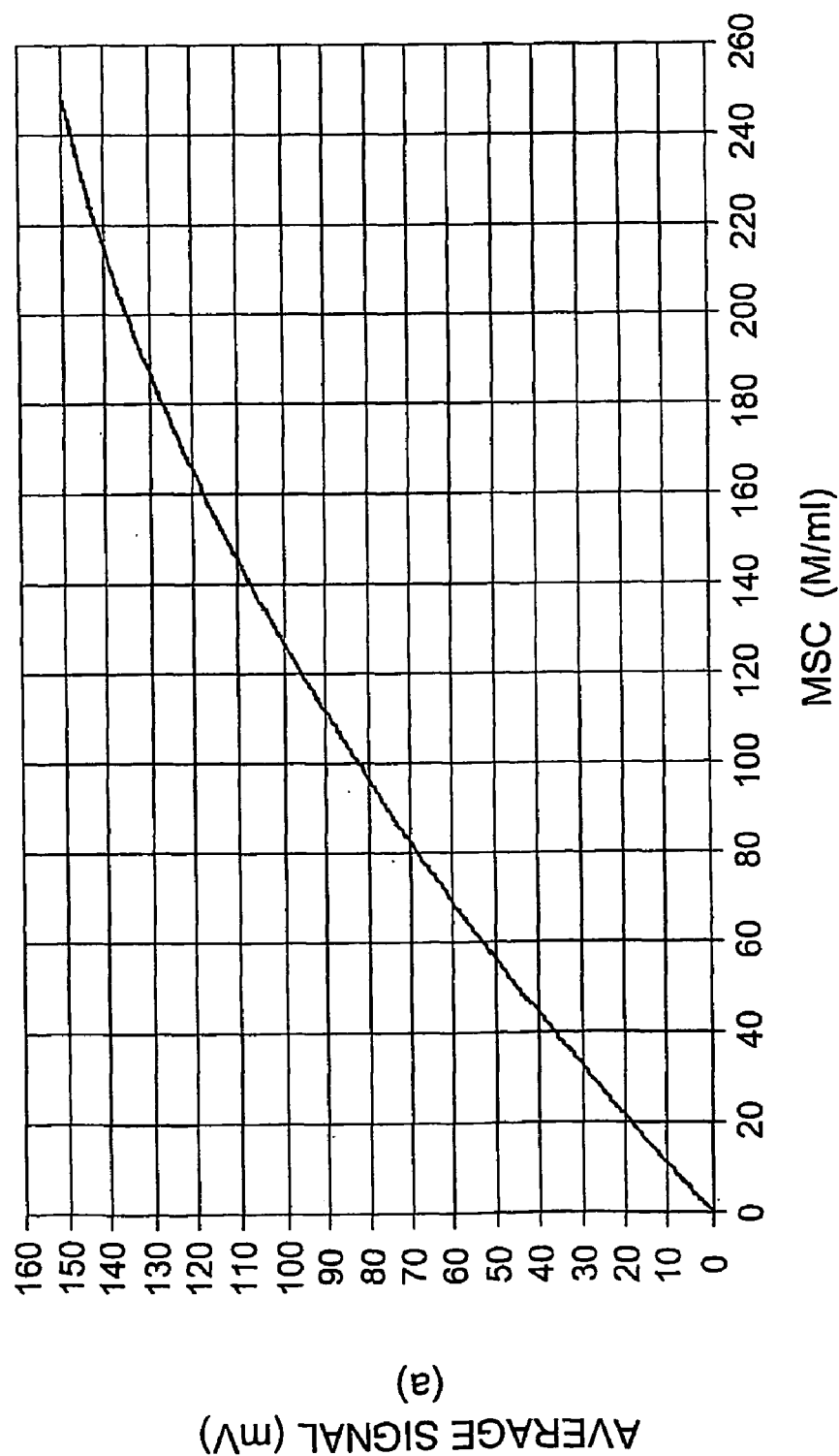
FIG. 9 is a correlation curve of the MSC with average analog signal.

With reference to FIG. 9, a specific human sperm sample was analyzed in accordance with the invention. It was found that the dependency of MSC on a could be described by the following algebraic expression:

$$MSC = 0.0047a^2 + 0.869a \qquad (I)$$

A good linear correlation was found to exist for small values of a. Using formula (I), the correlation factor (r) for fresh sperm over the entire range was >0.98.

Analysis of treated semen samples with varying viscosity was also performed using thawed samples, washed sperm, diluted samples (both in 3% Sodium Citrate and Test Yolk buffer) as well as with samples containing up to 20% glycerol having artificially raised viscosity. It was found that varying sample viscosity (and therefore sperm velocity), did not significantly affect the correlation between MSC and average signal ("r" in all case remained above 0.96).

Using centrifugal enrichment techniques, a very wide range of motile human sperm concentrations were measured (up to 250 M/ml). No significant saturation was found. The slight non-linearity at the highest ranges is easily corrected by a simple second-degree polynomial correction—given above.

Analysis of bovine semen was also carried out and correlation factors between bovine MSC and identically averaged signals (same methodology as for humans) provided similarly excellent results. It is to be noted however, that bovine semen has to be diluted prior to measurements. This is due to their MSC being typically an order of magnitude above that of human.

EXAMPLE 4

Figure 7:
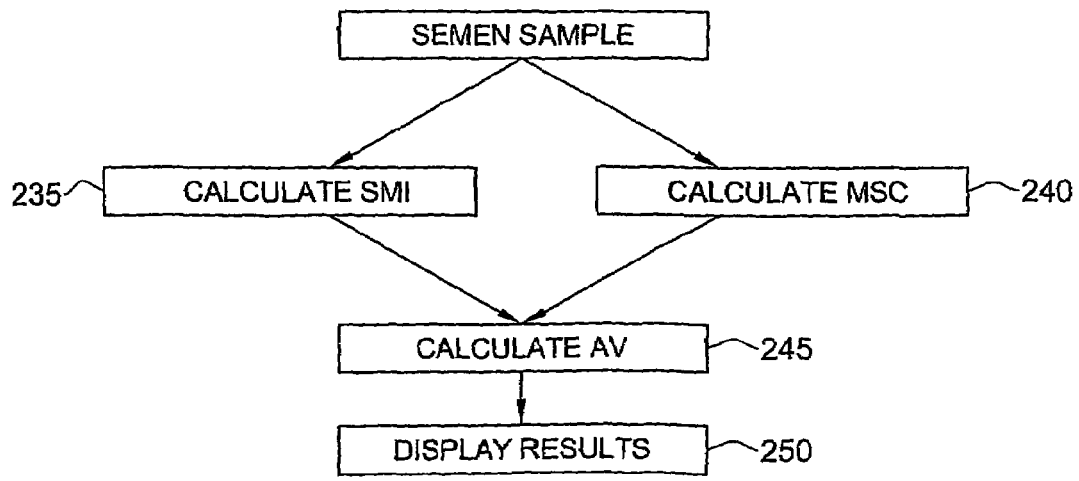
FIG. 7 is a flow chart illustrating an algorithm for calculating the average velocity.

As explained above, the average velocity is a function of SMI and MSC. With reference to FIG. 7, the SMI is calculated in step 235. This may be done, for example, as disclosed in U.S. Pat. No. 4,176,953, or using an SQA analyzer. In step 240 the MSC is calculated by any known method. In a preferred embodiment, MSC is calculated by the algorithm of the invention (see Example 3 above). In step 245 the average velocity AV is calculated using an algebraic expression involving the ratio SMI/MSC. In one embodiment AV is calculated using the algebraic expression:

$$AV = 0.001\left(\frac{SMI}{MSC}\right)^3 + 0.1\left(\frac{SMI}{MSC}\right)^2 + 0.89\left(\frac{SMI}{MSC}\right)$$

In step 250 the results are displayed on the display device 145 or 148 (FIG. 5).

EXAMPLE 5

Figure 10:
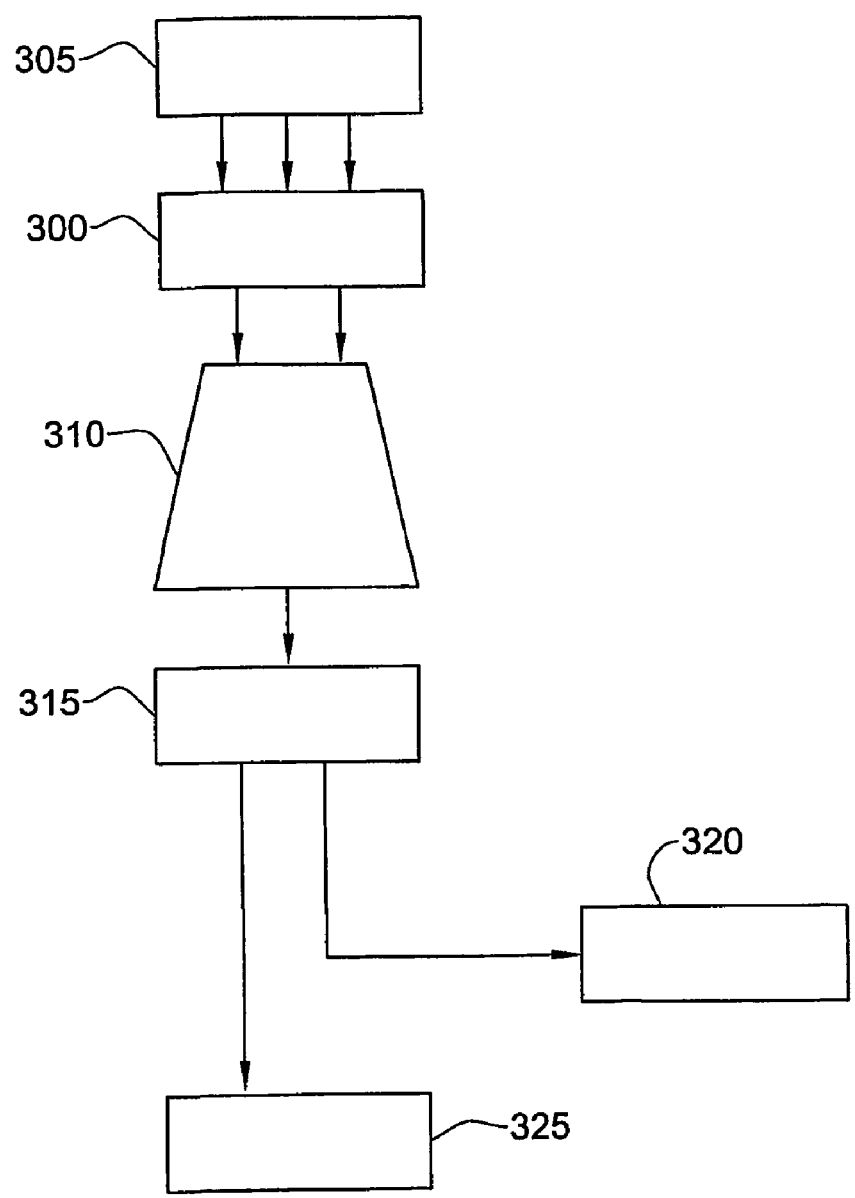
FIG. 10 is a block diagram illustrating one embodiment of a video visualization system according to the invention.

One embodiment of a video visualization subsystem (VVS) which may be used with the analyzing system of the invention is illustrated in FIG. 10. A semen sample 300 is placed before a diffused, phase contrasted illuminator 305. The sample may be held in a standard laboratory slide or smear, or may be held in a sampling device according to the invention. Light from the illuminator 305 passes through the sample 300 and through a switchable dual lens system 310, preferably with amplifications of 20 and 40. The amplified light is then conveyed to a miniature CCD video camera 315. The resulting image may be displayed on a built-in internal viewing screen 320 or on external displaying means 325 such as PCs, screens, printing devices, etc.

In a preferred embodiment, the VVS is built around the sampling device of the invention, and particularly the thin measuring compartment. The object of this feature is that no extra preparations will be necessary to incorporate this function to the normal testing procedure. One simply takes the semen filled device on which the automated test is performed and inserts it—as such, into the viewing port. However, the VVS is not limited to use with the sampling device of the invention, and may be used with standard laboratory slides or smears.

The front end of the VVS is similar to that of the microscope. Two objective lenses are selectable for optimizing magnification and field of view, according to the application (×20 or ×40). However, instead of the eyepieces of the microscope, the image from the objective is conveyed to a miniature CCD video camera. The size of the CCD (diagonal) is 6 mm. The viewing screen is a 100 mm LCD. This provides a video amplification of app. 17. This in effect gives a potential overall amplification of 340 or 680. Although amplification factors of only 200 and 400 are required, this set up is selected so that the above amplification could be reached in a much smaller construction. This is desirable e.g. for a compact and robust desk-top unit (decreasing the specified image distance decreases the amplification to what is required).

The lenses and their magnification set-up may be selected so that the "Working distance" (from object to lenses) can be varied to enable scanning throughout the whole depth of the thin measuring compartment (e.g. 300 microns). This is opposed to normal microscopic viewing which does not require such scanning, because the object is normally enclosed in a slide which is just 20 microns deep and the whole depth can be viewed without scanning or refocusing.

As mentioned above, an overall amplification factor of 200 or 400 may be selected. An amplification of 400 will be the choice when it is necessary to identify non-spermic cells (white blood cells, round cells, etc.), as well as to investigate and evaluate various morphological pathologies of sperm cells (agglutinations, immature cells, sperm head or tail defects, etc.). An amplification of 200 will be preferable for cell counting—irrespective of whether they are sperm or others. The lower amplification provides a larger field of view (4 times larger) and thereby improved counting statistics. The possibility of freezing images greatly enhances both applications.

In order to facilitate cell counts and acquire a truly quantitative result using the VVS, in a preferred embodiment a calibrated grid may be charted directly on the LCD viewing screen. The grid comprises 2 cm squares which are equivalent to a pre-amplification size of 0.1 mm in the semen filled measuring compartment (amplification factor of 200). This approach precludes the very difficult task of precisely charting a minute grid on the measuring compartment itself. The latter expensive solution is incorporated in the Mackler Counting Chamber as well as some other hemacytometers—precluding their use as disposables. In the present invention this is unnecessary and the VVS allows the grid to be a part of the viewing screen.

The VVS may be useful in the following applications:
(a) Measuring very low sperm concentrations.
(b) Identifying foreign cells in the semen (other than sperm cells).
(c) Manual morphology analysis according to any selected criteria.
(d) Vasectomy efficacy validation.
(e) Diagnosing Azoospermia.
(f) On the spot comparison of computerized results with visual analysis.
(g) Providing hard copy "Snap shots" of immobilized images of various semen layers. The immobilization is achieved by electronic freezing of the images.

The invention claimed:

1. A sampling device for use in optically analyzing a biological fluid comprising:
   (i) an aspirator for aspirating the fluid into the device;
   (ii) a thin measuring chamber having an upper and lower wall, the distance between said walls being in the range of 100-500 microns;
   (iii) a thick measuring chamber having an upper and lower wall, the distance between said walls being in the range of 0.5-3 cm; and
   (iv) means for excluding air from said measuring chambers; wherein the upper and lower walls of said thin and thick measuring chambers are transparent and the thin measuring chamber and the thick measuring chambers are in fluid communication.

2. A sampling device for use in optically analyzing semen, the sampling device comprising:
   (i) an aspirator for aspirating semen into the device;
   (ii) a thin measuring chamber having an upper and lower wall, the distance between said walls being in the range of 100-500 microns;
   (iii) a thick measuring chamber having an upper and lower wall, the distance between said walls being in the range of 0.5-3 cm; and
   (iv) means for excluding air from said measuring chambers; wherein the upper and lower walls of said thin and thick measuring chambers are transparent and the thin measuring chamber and the thick measuring chambers are in fluid communication.

3. A device according to claim 1 wherein the distance between said walls of said thin measuring chamber is in the range of 250-350 microns.

4. A device according to claim 1 wherein the distance between said walls of said thick measuring chamber is in the range of 0.8-1.2 cm.

5. A device according to claim 1 wherein said aspirator comprises a cylinder and a plunger.

6. A device according to claim 1 wherein said means for excluding air comprises a valve positioned in between said measuring chambers and said aspirator.

7. A device according to claim 1 further comprising an adapter for aligning the device in an optical instrument.

8. A device according to claim 1 which is disposable.

* * * * *